Figure 2:
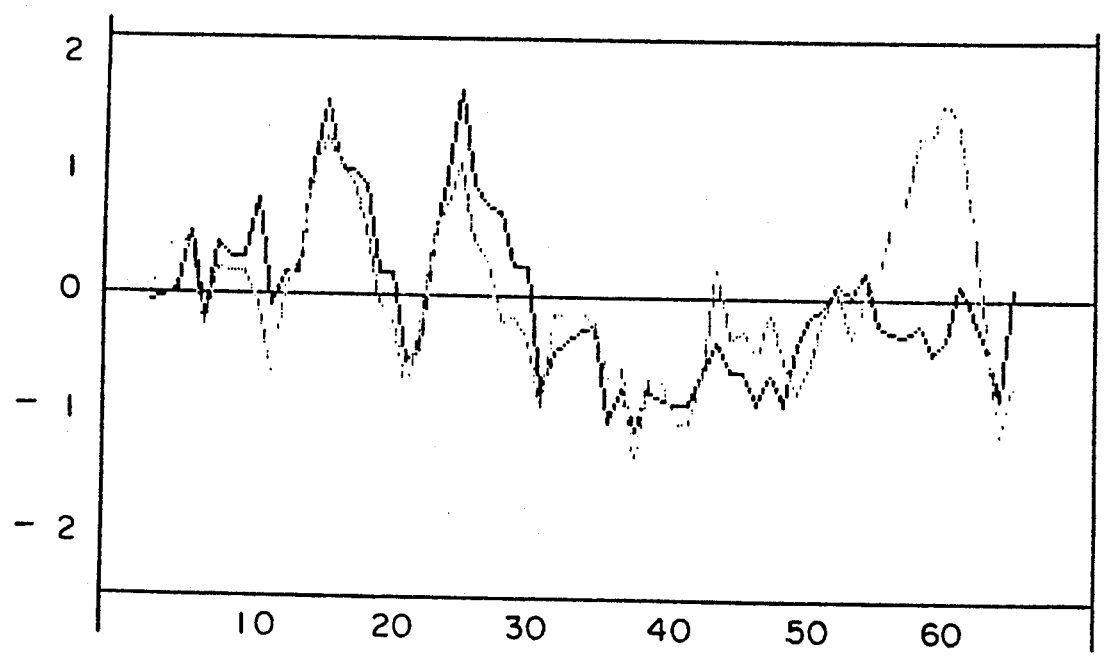
Figure 3A:
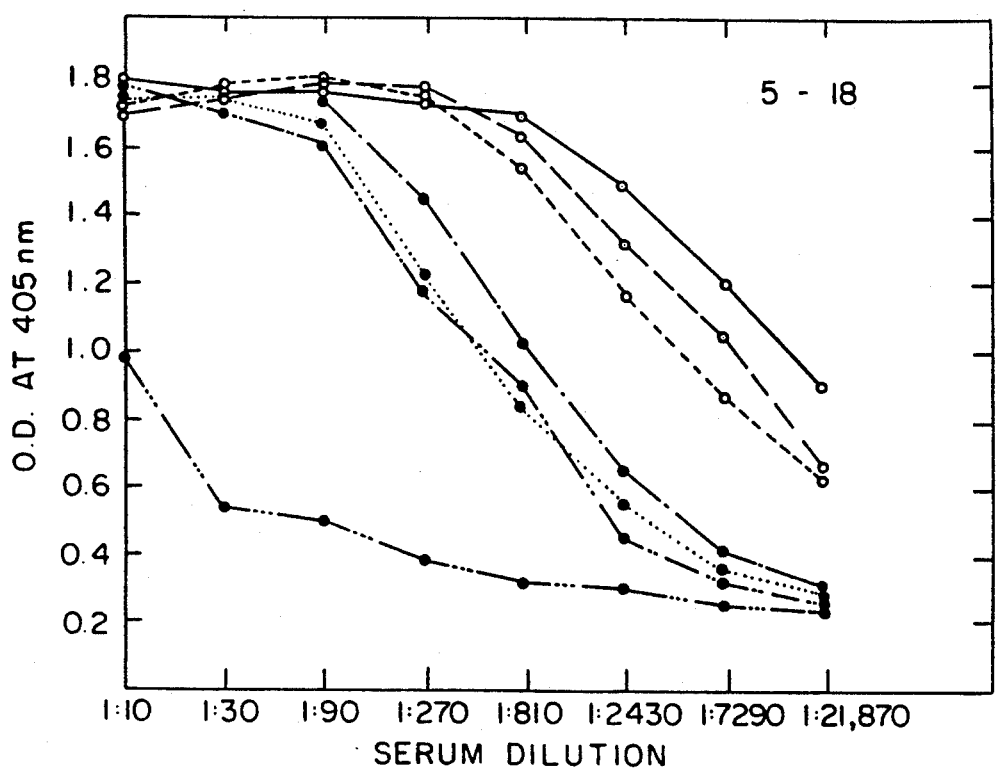
Figure 3B:
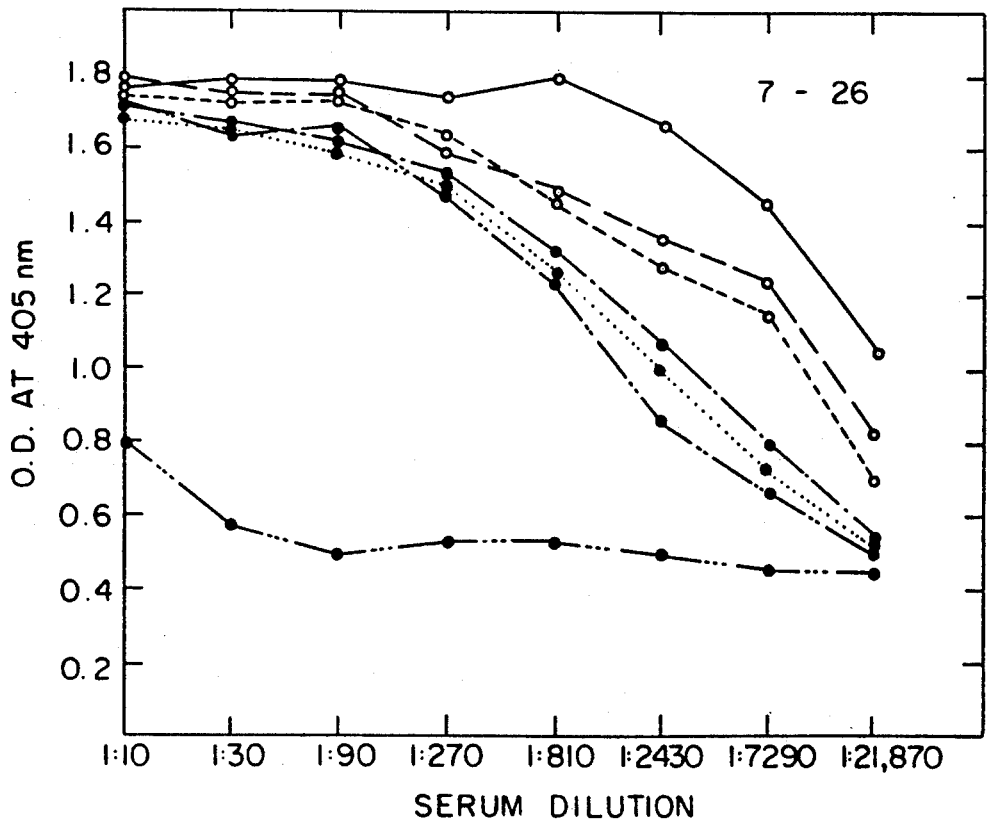
Figure 3C:
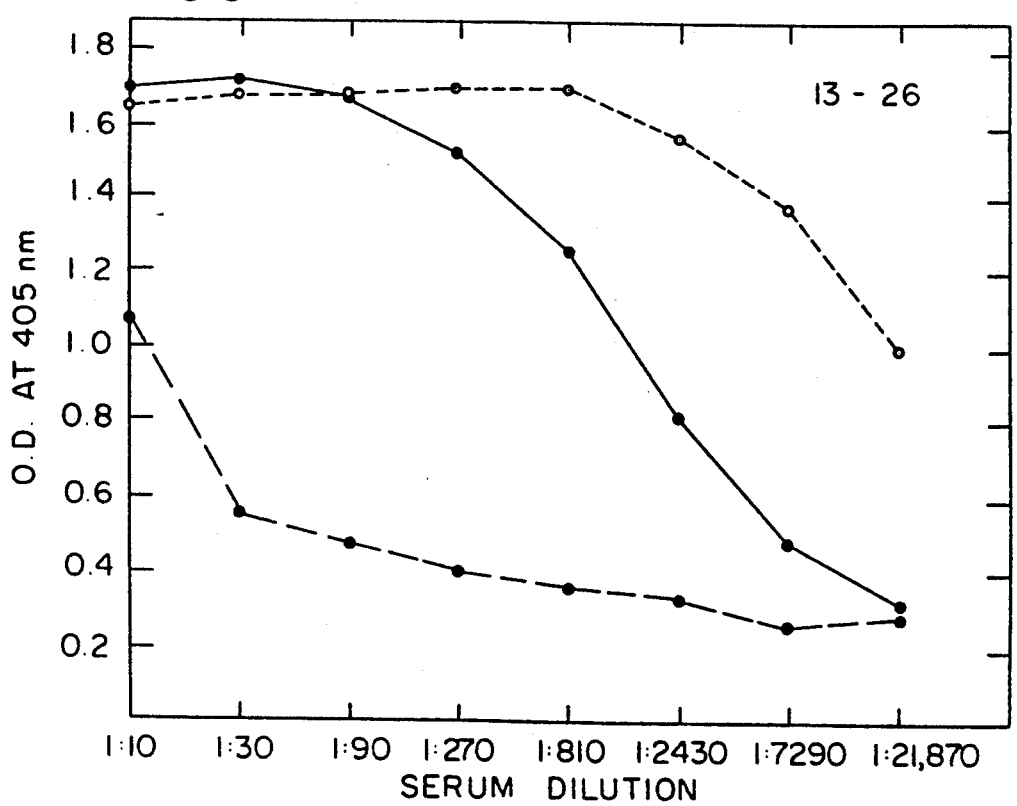
Figure 3D:
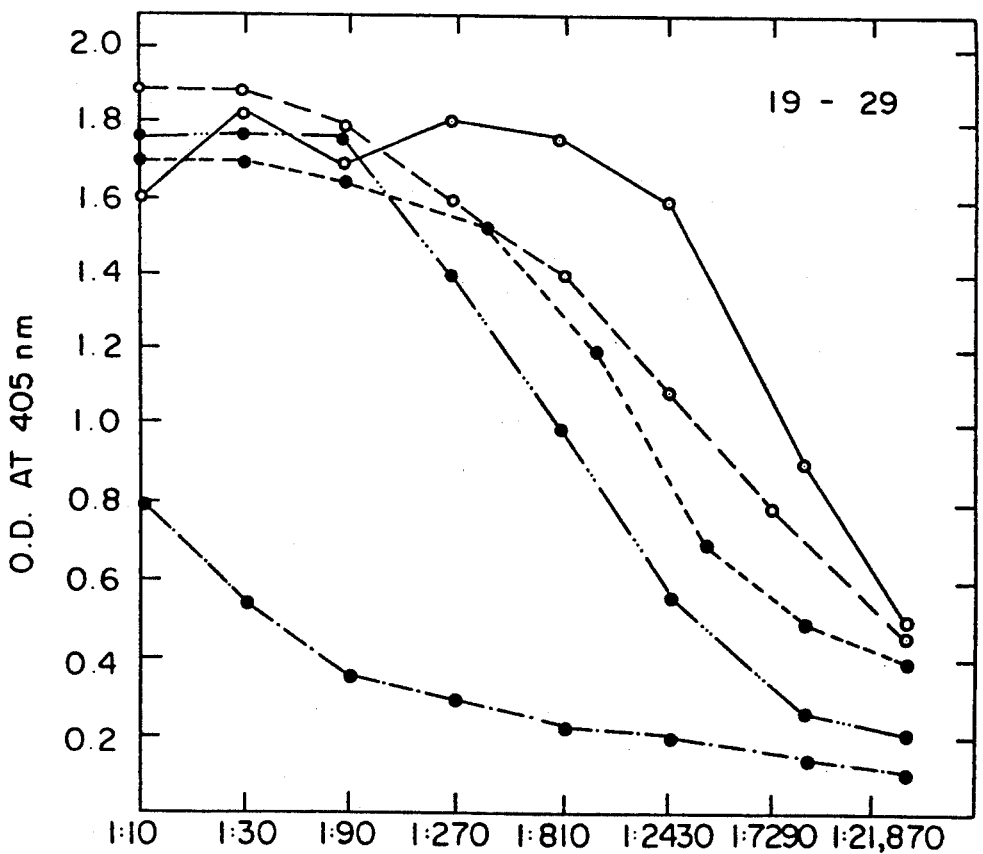

US005204097A

United States Patent [19]
Arnon et al.

[11] Patent Number: 5,204,097
[45] Date of Patent: * Apr. 20, 1993

[54] SHIGA TOXIN B CHAIN POLYPEPTIDES AND VACCINE THERETO

[75] Inventors: Ruth Arnon, Rehovot; Ilana Harari, Kfar Aviv, both of Israel; Gerald T. Keusch, Lexington; Arthur Donohue-Rolfe, Sudbury, both of Mass.

[73] Assignee: Yeda Research and Development Company Limited, Rehovot, Israel

[ * ] Notice: The portion of the term of this patent subsequent to Jun. 20, 2008 has been disclaimed.

[21] Appl. No.: 364,506

[22] Filed: Jun. 9, 1989

Related U.S. Application Data

[63] Continuation of Ser. No. 70,243, Jul. 6, 1987, abandoned.

[30] Foreign Application Priority Data

Jul. 6, 1986 [IL] Israel .................. 79346

[51] Int. Cl.$^5$ .................. A61K 39/02; C07K 7/00; C08H 1/00
[52] U.S. Cl. .................. 424/92; 530/323; 530/326; 530/327; 530/328; 530/345; 530/402; 530/403; 530/404; 530/405; 530/825; 424/88; 527/200; 527/202; 514/2; 514/13; 514/14; 514/15
[58] Field of Search .................. 530/326, 327, 345, 323, 530/328, 402-405, 825; 424/88, 92; 514/2, 13-15; 527/200, 202

[56] References Cited

U.S. PATENT DOCUMENTS 4,554,101 11/1985 Hoff .................. 424/88
4,751,064 6/1988 Sela et al. .................. 424/88

FOREIGN PATENT DOCUMENTS 0080806 6/1983 European Pat. Off. .................. 435/68

OTHER PUBLICATIONS

Regenmortel, *TIBS*, Jan. 1986, pp. 36-39.
King, C&EN, Apr. 1989.
Green et al, *Cell* vol. 28, 1982, pp. 477-487.
Kaiser et al, *Science* 223, 1984, pp. 249-255.
Seidah et al, *IBC* 261, 1986, pp. 13928-13931.
Brown et al *Inf and Immumt* 36(3) 1982, pp. 996-1005.
Yatsudo et al. CA vol. 105, 1986, #129165y.
Yatsudo et al. CA vol. 106, 1987, #134855y.
Alsnes et al, CA vol 101, 1984, #224039m.
Timmis et al, CA vol. 104, 1986, #15901j.
Bacterial Vaccines and Local Immunity, Nos. 1-2, 1986, pp. 125-130; I. Harari et al; "Synthetic Peptides of Shiga Toxin B-subunit Induce . . . ".
J. Exp. Med., vol. 160, Dec. 1984, pp. 1767-1781, the Rockefeller University Press; A. Donohue-Rolfe et al; "Pathogenisis of Shigella Diarrhea. IX. Simplified High Yield . . . ".

*Primary Examiner*—Garnette Draper
*Attorney, Agent, or Firm*—Browdy and Neimark

[57] ABSTRACT

The invention relates to a number of synthetic polypeptides which correspond to a part of the sequences of the Shiga B peptide chain. More specifically, the invention relates to polypeptides corresponding to the residues 5 to 18, 7 to 26, 13 to 26, and 19 to 29 of said B chain. The invention further relates to the conjugates of each of these with a suitable carrier and to polymers of each or these obtained by polymerization with a suitable polymerization agent: these can be used as effective vaccines which afford protection against Shiga toxin. Anti-peptide anti-sera are effective in neutralizing to a large extent the biological activity of Shiga toxin.

8 Claims, 8 Drawing Sheets

```
       1                   5                      10                    15
Thr-Pro-Asp-Cys-Val-Thr-Gly-Lys-Val-Glu-Tyr-Thr-Lys-Tyr-Asn- 20                     25                    30
       Asp-Asp-Asp-Thr-Phe-Thr-Val-Lys-Val-Gly-Asp-Lys-Glu-Leu-Phe- 35                     40                    45
       Thr-Asn-Arg-Trp-Asn-Leu-Gln-Ser-Leu-Leu-Leu-Ser-Ala-Gln-Ile- 50                     55                    60
       Thr-Gly-Met-Thr-Val-Thr-Ile-Lys-Gln-Asn-Ala-Cys-His-Asn-Gly- 65                     69
             Gly-Gly-Phe-Ser-Glu-Val-Ile-Phe-Arg
```

```
           1               5                  10                     15
Thr-Pro-Asp-Cys-Val-Thr-Gly-Lys-Val-Glu-Tyr-Thr-Lys-Tyr-Asn- 20                  25                     30
Asp-Asp-Asp-Thr-Phe-Thr-Val-Lys-Val-Gly-Asp-Lys-Glu-Leu-Phe- 35                  40                     45
Thr-Asn-Arg-Trp-Asn-Leu-Gln-Ser-Leu-Leu-Leu-Ser-Ala-Gln-Ile- 50                  55                     60
Thr-Gly-Met-Thr-Val-Thr-Ile-Lys-Gln-Asn-Ala-Cys-His-Asn-Gly- 65           69
Gly-Gly-Phe-Ser-Glu-Val-Ile-Phe-Arg
```

FIG. 1

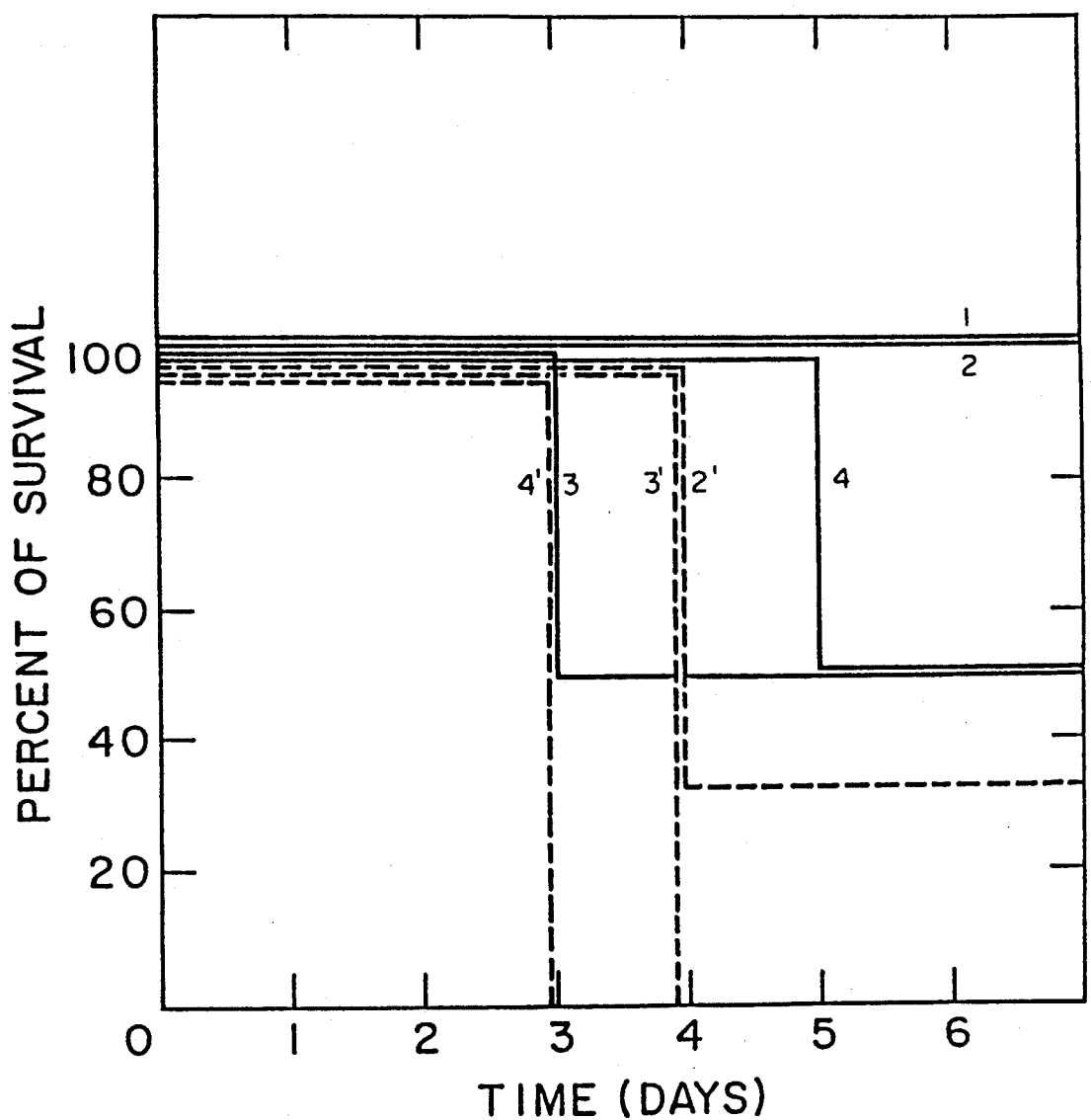

SHIGA TOXIN B CHAIN POLYPEPTIDES AND VACCINE THERETO

This application is a continuation of application Ser. No. 07/070,243, filed Jul. 6, 1987 now abandoned.

FIELD OF THE INVENTION

There are provided synthetic peptides corresponding to the sequences of the Shiga toxin B chain, consisting essentially of residues 5 to 18, 7 to 26, 13 to 26 and 19 to 29, respectively of the said B-chain, or to close analogs of these having biological activity. There are further provided conjugates of each of these with a suitable carrier, or polymeric forms thereof, such as polymers obtained by polymerization with glutaraldehyde.

Antisera against these interact with the homologous peptide and also with the intact protein.

There are provided vaccines based on such conjugates and polymeric forms. These confer a substantial degree of protection against Shiga toxin.

BACKGROUND OF THE INVENTION

Shiga toxin B chain is the binding subunit of the toxin, which has been purified and the amino acid sequence of this 6,500 dalton polypeptide was recently determined.

Vaccination against the Shigella bacillus and shigellosis presents several problems that have not been overcome in spite of many efforts. Some of the difficulties are inherent to the system of shigellosis. Pathogenesis in this case is generally considered to be related to the invasive properties of the organism (Genski, P et al., J. Infect. Dis 126:523 (1972)), the most clinically virulent species of which is *Shigella dysenteria l* (the Shiga bacillus). Most of the attempts towards Shigella vaccine preparation have been based on the expression of virulence-associated membrane antigens. Pathogenic strains of Shigella are known to produce a toxin, the role of which in the pathogenesis of shigellosis is rather controversial. However, the existence of toxin-neutralizing antibodies in the sera of convalescent patients may be indicative of the possibility to employ the toxin or its derivatives for introducing a protective immunity.

The toxin of *Shigella dysenteria l* (the "Shiga toxin") is known as one of the most potent of the lethal microbial toxins. It is classified as a neurotoxin due to its activity when parenterally administered to sensitive animals. It is also cytotoxic to certain tissue culture cells, as well as enterotoxic when applied to intestinal mucosa. This toxin has been purified and its structure was characterized as comprising two subunits, A and B, of Mr32,000 and Mr6,500, respectively (Donohue-Rolfe et al., J. Exp. Med. 160:1767 (1984)). Antibodies raised against the B subunit neutralized the cytotoxic effects of the toxin in HeLa cells monolayers and also inhibited the binding of labeled toxin to these cells, indicating that the B subunit is involved in the Shigella toxin binding to cell surface, see above reference.

In recent years it has been demonstrated that synthetic peptides corresponding to fragments of some bacterial toxins, when attached to appropriate carriers, can induce neutralizing an immune response towards the native toxin. This was shown for diphtheria toxin and for cholera toxin. In the latter case the antibodies elicited by a 15 amino acid residue fragment of the toxin's B chain neutralized also the heat-labile toxin of *E. coli*, which is homologous in its sequence to the cholera toxin.

SUMMARY OF THE INVENTION

The invention relates to synthetic vaccines against Shiga toxin. These are based on partial sequences of the B chain of this toxin, and more particularly on the sequences in the 5 to 18, 7 to 26, 13 to 26 and the 19 to 29 range of the B chain. The synthetic peptides in this, or close range, or slightly modified sequences, are conjugated with suitable carriers (such as tetanus toxoid or the synthetic copolymer pDGDL), or there are used polymerized forms of these peptides, such as those obtained by polymerization with gluataraldyde.

Antisera raised in laboratory animals, such as rabbits, against these conjugates or polymeric forms react with the homologous peptides and also with the intact protein.

Thus, there are provided vaccination means which can be used for the vaccination against Shiga toxin, or for the treatment of, and alleviation of symptoms of the results of such toxin in mammals, including humans.

The anti-peptide sera were quite effective in neutralizing all the biological activities of the Shiga toxin. Cytotoxicity was inhibited to an extent of up to 70%, as compared to 80% inhibition caused by antisera against the holotoxin. The enterotoxic activity i.e., the fluid secretion into ligated ileal loops in rats was neutralized to an extent of over 80% as compared to 90% neutralization by anti-shiga toxin, and the neurotoxic activity was also neutralized to a comparable level of neutralization effected by the anti-toxic serum. Moreover, active immunization of mice with the peptide-conjugates actually protected them against the lethal effect of the Shiga toxin.

During recent years an effort has been made to provide means for the prediction of protein antigenicity of parts of toxin polypepotides. Computer programs developed for this purpose, tended to detect certain polarity scales, to detect regions of high hydrophilicity, flexibility, thermolability, and acrophilicity along the sequence of the protein.

Although helpful, none of these makes it possible to predict with a high degree of confidence which of the parts of the toxin protein will be suitable as effective vaccine, and such calculations allow only to determine regions which have subsequently to be evaluated experimentally. In this present case hydrophilicity was used to try and predict which parts of the protein would be suitable for experimental purposes.

Various calculations and our previous experience led to the conclusion that there exists a good chance to obtain an effective polypeptide in the ranges of resides 5 to 18, 7 to 26, 13 to 26 and 19 to 29. This assumption was based, amongst others, on considerations of hydrophilicity on the one hand, and on high surface exposure. The profile of FIG. 2, represents hydrophilicity and surface area residues.

The peptides defined above encompass the N-terminal peak, with a few additional residues on either its amino or carboxy side. Two of the peptides contain in position 13 a tyrosine residue which was later discovered as a mistake in the sequence, to be replaced by lysine at this position. This could have had some effect on the reactivity of the anti-peptides sera with the intact Shiga toxin. This is more relevant to peptide 5 to 18 in which this position occupies the middle of the peptide, and could thus have a strong influence on its folding.

The region circumscribed by the high hydrophilicity/surface residues peak per se, i.e. the sequence 12-18, is definitely responsible to a significant level for the antigenic specificity of the antibodies elicited by the peptide 5 to 18, as it was capable of inhibiting the homologous peptide antipeptide interaction. However, other parts of the 5 to 8 peptide also contributed to the specifity, as the inhibition by the homologous peptide reached a higher level (100%).

EXPERIMENTAL

Animals: SPD rats (8-12 weeks old), and New Zealand rabbits were from the breeding house of the Weizmann Institute of Science. SJL and C57BL mice 4-5 weeks old, were purchased from Jackson Laboratories (Bas Harbor Me.).

Shiga Toxin: The toxin was purified from a total cell lysate of Shigella dysenteria, by column chromatography on Blue Sepharose followed by chromatofocusing, and final chromatography on Bio-Gel P-60, as described previously (Donohue-Rolfe 1984 ibid.). A and B subunits of the toxin were separated, after dissociation in 5% formic acid (Lai et al., J. Infect, Diseases 133:523 (1976)), as described (Donohue-Rolfe 1984 ibid.,).

Carriers: Tetanus toxoid (Mr150,000) was purchased from RAFA Laboratories (Jerusalem) and purified as a 15-30% saturation cut of $(NH_4)_2SO_4$ precipitation and then by column chromatography of Sephadex G-100. A linear copolymer (Mr60,000) of D-glutamic acid and -D lysine (pDGDL), and branched copolymer of L-tyrosine, L-glutamic acid, L-alanin and L-lysine (T,G)-A—L were purchased from Bio-Yeda (Rehovot, Israel).

Peptide Synthesis: Peptides were synthesized by the solid phase method (Merrifield R. B., J. Am. Chem. Soc. 85:2149 (1963)), modified, (Stewart, J. M., Young J. D., "Solid-phase peptide synthesis", Freedman W. H., Company, San Francisco (1969)), using t-butyloxycarbonyl (t-boc) derivatives of amino acid with their appropriate protecting groups. The side chains protecting groups were O-benzyl ether for threonine, dichlorobenzyl ether for tyrosine, carbobenzoxy for lysine, benzyl ester for aspartic and glutamic acids, and p-nitro phenyl ester for asparagine. The initial amino acid resin was prepared by esterification of the relevant t-butyloxy-carbonyl amino acid to chloromethylated resin (polystyrene-1% of divinylbenzene). The progress of synthesis was monitored by ninhydrin analysis. Two cycles of coupling were performed whenever the coupling reaction was <99% complete. The protecting groups were removed and the peptides were cleaved from the resin at 0° C. with anhydrous hydrogen fluoride containing scavengers as 10% anisole and 1% 1,2-ethanedithiol. Crude peptides recovered after cleavage from the resin were purified on Sephadex G-15 column. The purity of peptides was established by amino acid analysis, using a D-500 amino acid analyzer (Durrum).

Conjugation of peptides to the carriers:

1-Ethyl-3(3'-dimthylaminopropyl) carbodiimide hydrochloride was used as a coupling agent and the conjugation was proceeded as described previously: (Muller, G. M. et al., Proc. Natl. Acad. Sci. U.S.A. 79:569 (1982)). In addition to the conjugates, a polymer of each peptide was prepared using 0.1% glutaraldehyde (Audibert et al., Nature 289:593 (1981).

Immunization Procedures:

(A) Anti-shiga toxin: Purified Shigella toxin was converted to toxoid by formalin treatment, and the toxoid which contained <1% of the original cytotoxic activity was used for immunization of rabbits in complete Freund's adjuvant (CFA).

Anti-peptide antibodies:

Rabbits were immunized by multi-site intradermal injections of 1 mg of the appropriate conjugate in CFA.

Mice were immunized by foot pad injections with 100 ug of the conjugate, in CFA, followed by two booster injections in incomplete adjuvant.

Enzyme-labeled immunosorbent assay (ELISA):

Modified procedure of micro ELISA was performed on antigen coated (0.5-1 μg per well) flat bottom microtiter plates (precoated with 0.2% glutaraldehyde whenever peptides were used as antigen), by addition of a 3-fold serial dilution of the tested serum, followed by β-galactosidase conjugate of protein A (Amersham). After addition of the substrate (O-nitrophenyl-β-D-galactopyranoside) the plates were read in an automatic reader (Titertek Multiskan, Flow Laboratories).

Immunoblotting:

Shiga toxin, separated into its subunits on a 5-15% SDS-polacrylamide gel, was transferred to a nitrocellulose sheet. To reduce non-specific binding of the antiserum, the blot was incubated for 1 h with 9 mM Tris-HCl buffer (pH 7.4) containing 0.9% NaCl and 3% (w/v) bovine serum albumin and then was cut into strips. The strips were incubated for 3 h at room temperature with a 1:50 dilution of the various antisera. After thorough washing, the strips were incubated for 2 h with [$^{125}$I] labeled goat anti-rabbit IgG ($5 \times 10^5$ cpm/ml). The washed and dried blots were autoradiographed.

Cytotoxicity Assay:

Cytotoxicity to HeLa cells performed by employing the extent of HeLa cell detachment as the indicator of the cytotoxicity of Shiga toxin. HeLa cells (line CCL2) were maintained at 35° C. in growth medium consisting of Eagle minimum essential Earle Salts, supplemented with 10% heat-inactivated fetal bovine serum, 2 mM glutamine, 180 U of penicillin per ml, and 0.18 mg of streptomycin per ml in 5% $CO_2$ atmosphere. To establish monolayers, freshly trypsinized cells were suspended at a concentration of $2.5 \times 10^5$ cells per ml in growth medium, and 0.10 ml samples were dispensed into 96-well microtiter plates (Costar, Cambridge, Mass). Cells were allowed to attach for 10 to 20 h before experimental use. Serial dilutions of samples were added (0.10 ml) and the plates were incubated for an additional 18 h. The end-point of toxin activity was determined by fixing and staining with crystal violet formaldehyde solution. Stained cell monolayers were dissolved in 50% ethanol containing 1% sodium dodecyl sulfate, The absorbance (595 nm) of the extracts was determined with microtiter plate colorimeter. The toxin dilution resulting in 50% cell detachment ($CD_{50}$), i.e., 50% dye uptake, was chosen as an appropriate endpoint for the assay.

Inhibition of cytotoxicity was determined by incubating serial dilutions of rabbit antisera in 37° C. for 1 h in the presence of an equal volume of Shiga toxin in the predetermined dilution. Duplicates of 0.1 ml asamples of toxin-antitoxin mixtures were incubated with cell monolayer for toxicity assay as described above.

Ligated ileal loop assay:

The assay was carried out as follows: SPD rats were starved for 24 h and then anesthetized with ether; their abdomens were opened and the small intestine was ligated in 2-3 cm long loops. The loops were injected with 1-10 μg of Shiga toxin in PBS. Control loops were injected with the same volume of PBS alone. The abdomen was then closed. Food and water were withheld and animals were sacrificed after 12 h. Fluid accumulation per centimeter of loop was determined by measuring the length and weight of each loop.

For inhibition assays, the toxin was pre-incubated for 1 h with a 1:25 dilution of the anti-peptide sera before injection into the loops. Every rat included both negative and positive controls, namely, loops injected with PBS alone and Shiga toxin in PBS, respectively.

Neurotoxic activity:

Toxin lethality to mice was assayed by intraperitoneal injection of various amounts (0.1–0.3 μg) of toxin into groups of mice. From cumulative death during 7–8 days, 50% lethal doses were calculated. Toxin was diluted in PBS and injected in volumes of 200 μl per mouse. Neurtalization of neurotoxicity was determined by introperitoneal injection of toxin previously incubated with a 1:10 dilution of the antiserum for 30 min at 37° C. Injections of toxin alone and PBS alone were used as controls.

Results:

Predicition and synthesis of antigenic peptides of the Shiga toxin B-unit:

The hydrophilicty pattern of the molecules as well as the regions containing high contents of surface residues was derived from the amino acid sequence (FIG. 1) according to a computer program prepared in our laboratory and based on values assigned to each amino acid residue by Hopp, (personal communication). The profiles of both hydrophilicy and surface residues depicted in FIG. 2, demonstrate that in the N-terminal region, the segment between residues 12 and 22 represents a peak in which high hydrophilicity and high contents of surface residues coincide.

Based on the above, two peptides were synthesized corresponding to sequence 5–18 and 13–26 of the molecule, encompassing the hydrophilicity peak, plus a few amino acid residues on either its amino- or carboxy-terminus, respectively. Furthermore sequences 7 to 26 and 19 to 29 were synthesized. The peptides were purified by gel filtration on Sephadex G-15, and analyzed for their amino acid contents.

Preparation and characterization of conjugates:

Each of the peptides was conjugated to tetanus toxoid and to the synthetic copolymer pDGDL. The contents of the coupled peptide in each conjugate were determined by amino acid analysis, in comparison to the composition of the carrier alone. The various conjugates are listed in Table I. As shown the number of moles of peptide attached per mole of carrier ranged between 20 and 38.

Antibodies to the synthetic peptides:

Each of the conjugates and polymers of the peptides was used for immunization of four rabbits and all the antisera were evaluated by ELISA for their interaction with the respective homologous peptide, as well as with the intact Shiga toxin. The range of titers of the various antisera with the intact toxin is given in Table I. Those individual antisera that showed the highest reactivity with the respective peptide, as well as cross-reactivity with the toxin, were used in all further analyses and assays. In the case of the anti 5–18 peptide, the highest titer was obtained by using the conjugate with pDGDL as a carrier, whereas in the case of the peptide 13–26 the highest response was induced by the polymer of the peptide.

Figure 4:
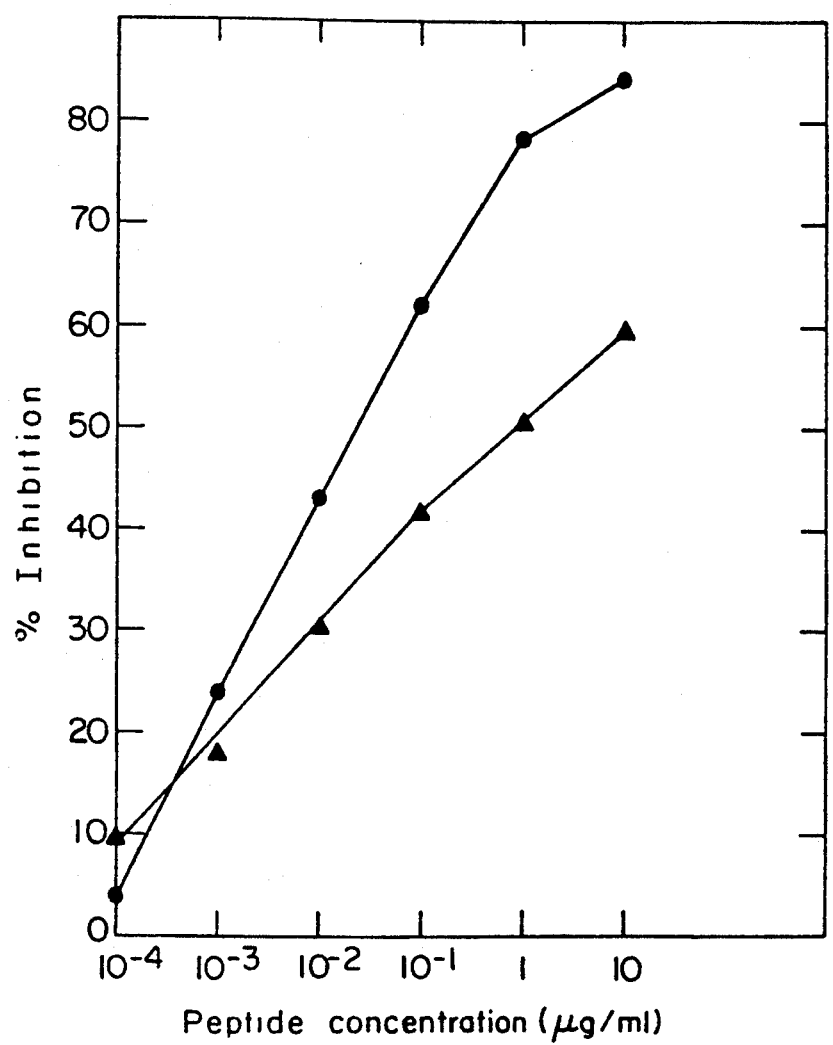

A) ELISA:

The reactivity of each of the antisera was assayed by ELISA against both the homologous peptide and the intact shiga toxin is illustrated in FIG. 3. As shown, both antisera contained a significant level of antibodies against the respective homologous peptide detectable antibodies up to a dilution of 1:2,500 and also showed a high cross-reactivity with the intact shiga toxin, comparable in its level with the homologous peptide-anti-peptide reaction. The specificity of this reaction is partially towards the segment of residues 12–18, since this peptide could efficiently inhibit the ELISA reaction (FIG. 4).

B) Immunoblotting:

The interaction of the anti-peptides sera with the intact Shiga toxin was determined by immunoblotting. Both the subunits are of course recognized by antiserum against the intact Shiga toxin. The antisera against either of the synthetic peptides, (peptide 5 to 18, and peptide 13 to 16), did not react at all with the A subunit, but recognized the B subunit. A higher molecular weight band represents probably an oligomer of the subunit.

Neutralization of biological activity of the Toxin.

Figure 5:
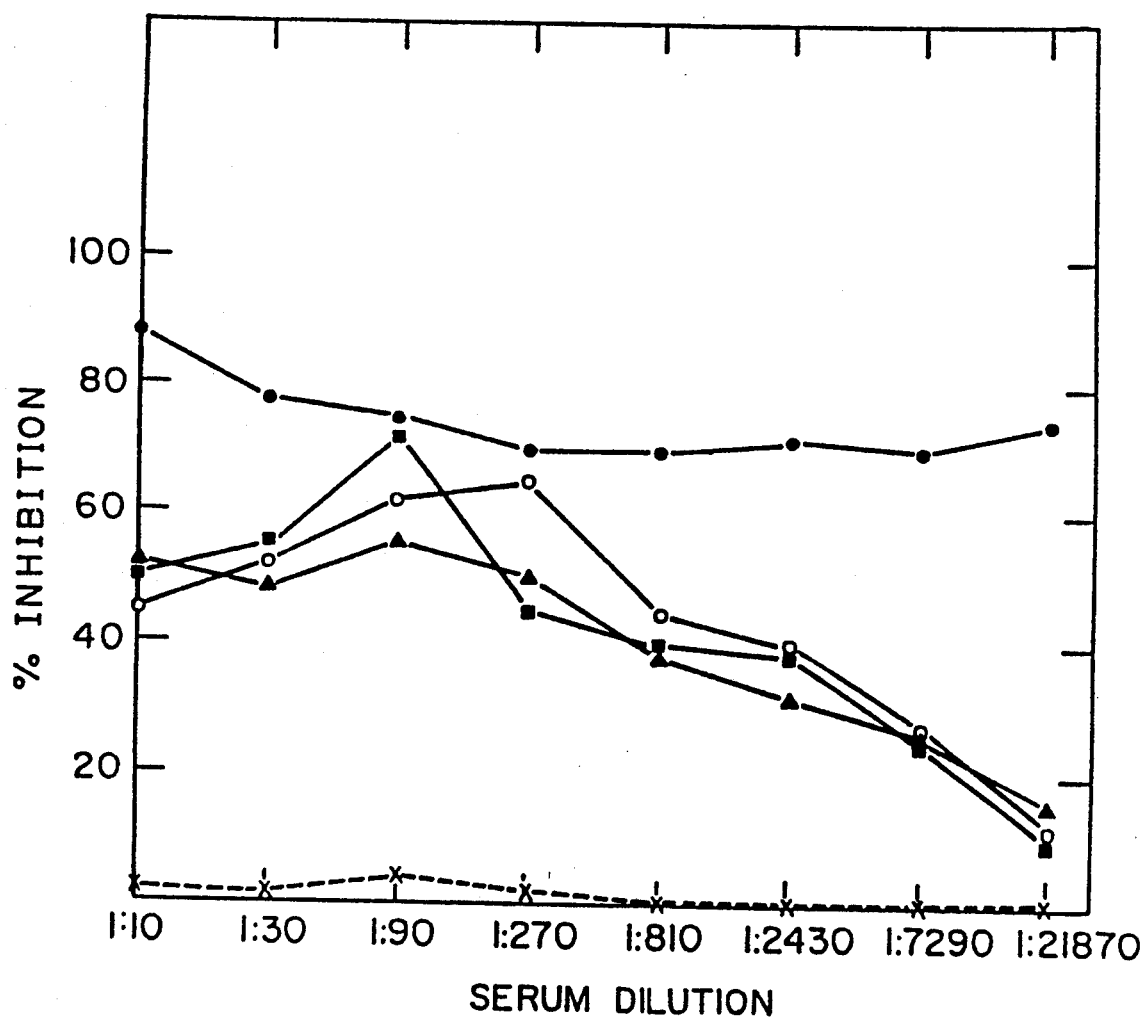

The cytotoxicity of the Shiga toxin was determined by the decrease of the viability of HeLa cells in its presence. In most experiments the toxin, at concentration of 500 pg per well, caused high mortality of the cells, a value which was taken as zero inhibition. (For the calculations, the absorbance of the lysed cells in absence of toxin was taken as no mortality, or 100% inhibition). Preincubation of the toxin with the various antisera resulted in inhibition of the cytotoxic effect, as shown in FIG. 5. The highest effect was brought about by the antiserum against intact shiga toxin, which led to approximately 80% inhibition even at a dilution of 1:20,000. The antisera against both peptides 5 to 18, 7 to 26, 13 to 26, and 19 to 29 led to significant inhibition of the cytotoxicity, up to a level of 50–70%. This effect was, however, concentration-dependent, and dimished at serum dilution 1:100 or above.

Figure 6:
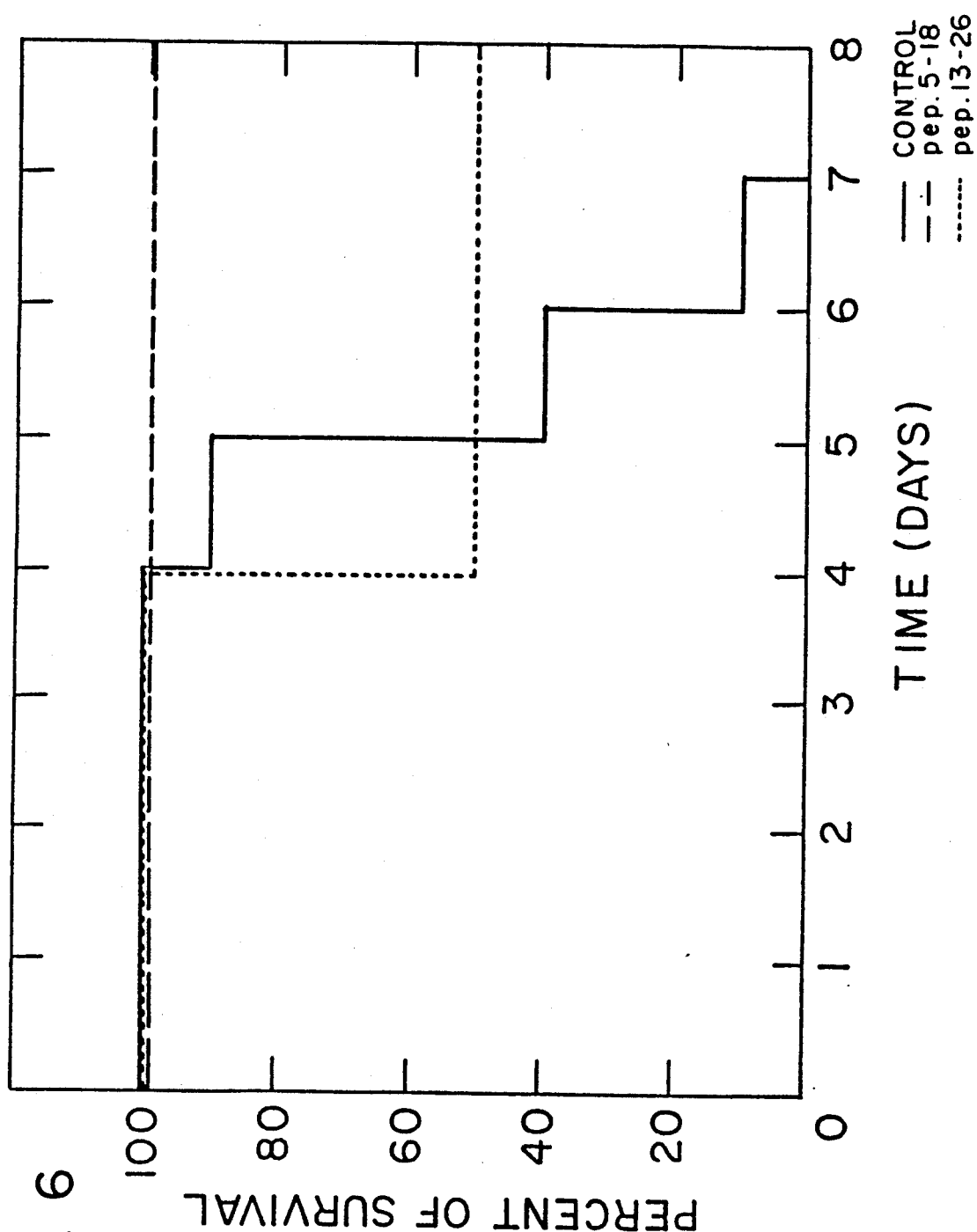

The enterotoxic activity of Shiga toxin, as measured by fluid secretion into ligated intestinal loops of rats, was also effectively inhibited by the anti-peptide sera. As is shown in Table II, antisera against either peptide were effective, with anti-peptide 5 to 18 showing the same level of neutralization as anti-Shiga toxin. Similar results were obtained with the anti-sera against the other three peptides. The neurotoxic activity of the Shiga toxin was measured by the lethal effect on mice caused by three different doses of the toxin ranging from 0.15 to 0.25 μg. As shown in FIG. 6 antiserum against peptide neutralized completely the toxicity caused by 0.15 μg, and led to partial neutralization of higher doses of the toxin.

Protection against neurotoxic activity of shiga toxin:

Active immunization of mice with the peptide conjugate 5 to 18-pDGDL and the 13 to 26 polymer led to their protection against the neurotoxic activity of the Shiga toxin. As shown in FIG. 7, all unimmunized mice challenged with 0.15 μg of the toxin died within 7 days, whereas all those immunized with the 13 to 26 polymer survived a similar challenge. Immunization with conjugates of the other peptides lead to partial protection.

The antibodies induced by either of the peptides according to the invention are of value since they definitely recognize a structure very similar to that assumed by the corresponding regions in the intact toxin. This is manifested by the almost identical interaction of the sera with the peptide and the intact toxin in the ELISA assay. However, the most significant finding in this study, is the high neutralization capacity exerted by the antibodies elicited by both synthetic peptides. Concerning the inhibition of the cytotoxicity to HeLa cells, the anti-peptide antibodies (at a dilution of 1:100) can actually lead to 80% inhibition, similar to that caused by antibodies to whole Shiga toxin. Even though the latter is of higher inhibitory capacity, as emerges from the high dilutions at which it is still active, this finding is meaningful.

The extent of neutralization of the enterotoxic activity of the toxin by the antisera to the two peptides, at a 1:25 diltuion, is almost as high as that caused by the anti-Shiga toxin (Table II), and so is the neutralization of the neurotoxic activity (FIG. 6). In the latter case, the anti-peptide serum at a 1:10 dilution prevented completely the lethal effect of 0.15 μg toxin, and led to partial neutralization of the toxic effect on 0.2 μg toxin. In comparison, anti-Shiga toxin at the same dilution overcame the lethal effect of 0.2 μg toxin.

Of most promise, in the context of the potential development of synthetic vaccines, is the protective efficacy against the lethal neurotoxic effect of Shiga toxin, brought about by active immunization with the peptides conjugates (FIG. 7). The conjugate of peptide 13 to 26 led to full protection in 20 mice. It is realized by now that in the case of Shigella, it is probably impossible to prepare a vaccine based solely on the toxin, since toxoid vaccines employed to date do not provide adequate protection against infection. The membrane antigens of the bacteria which, as mentioned earlier, are associated with its virulence and invasiveness to the colonic epithelium, will probably serve as the main component for any Shigella vaccine, whether killed or live, conventional or genetically engineered. However, the availability of synthetic peptide(s) which have no toxic effect of their own, and yet can elicit protection against the damaging and lethal effects of the toxin, could be an important additional ingredient to be considered in the design of Shigella vaccine.

Legend to the figures:

FIG. 1 Shows the amino acid sequence of Shigella toxin B subunit.

FIG. 2. A computerized plot depicting surface residues and hydrophilicity if the Shiga toxin B subunit according to its amino acid sequence.

FIG. 3a–3d The four peptides 5 to 18, 7 to 26, 13 to 26 and 19 to 29 were conjugated with different carriers, each conjugate was injected to 4 rabbits and antisera were tested for recognition of the homologous peptide and native protein by ELISA. o, reaction with homologous peptides; •, reaction with intact shiga toxin. Lowest curve in each section—reaction of preimmune serum.

FIG. 4. Illustrates inhibition of anti-peptides sera by homologous and non-homologous peptide.

FIG. 5. Illustrates inhibition of the cytotoxic activity of 500 pgr shiga toxin on HeLa cells by the anti-peptide sera.

FIG. 6. Neutralization of the neurotoxic activity of different concentration shiga toxin in C57B1 mice. Each group (10 mice) was injected either with toxin alone or toxin mixed with 1:10 dilution of the respective antiserum.

FIG. 7. Protection of mice (SJL) by immunization with respective peptides conjugate in CFA. Seven days following the second booster immunization, the mice (20 per group) were challenged by an injection of 150 ng toxin and their survival compared with a control group of toxin challenged immunized mice.

TABLE I

| Peptide | Carrier | Coupling Reagent | Content of Peptide mole/mole |
|---|---|---|---|
| 5–18 | Tetanus Toxoid | EDCI | 36 |
| 5–18 | (T,G)-A-L | EDCI | 38 |
| 5–18 | Poly-D-glu-D-Lys | EDCI | 26 |
| 5–18 | Polymerized | Glutardialdehyde | Mr. 60,000 |
| 7–26 | Tetanus Toxoid | EDCI | 35 |
| 7–26 | Poly-D-glu-D-Lys | EDCI | 20 |
| 7–26 | Polymerized | Glutardialdehyde | Mr. 60,000 |
| 13–26 | Tetanus Toxoid | EDCI | 34 |
| 13–26 | (T,G)-A-L | EDCI | 33 |
| 13–26 | Poly D-glu-D-Lys | EDCI | 20 |
| 13–26 | Polymerized | Glutardialdehyde | Mr. 80,000 |
| 19–29 | Tetanus Toxoid | EDCI | 30 |
| 19–29 | Poly D-glu D-Lys | EDCI | 18 |
| 19–29 | Polymerized | Glutardialdehyde | Mr. 40,000 |

TABLE II

NEUTRALIZATION OF ENTEROTOXIC EFFECT[a]

| Antiserum | Weight (gr per 1 cm loop) | | | % Inhibition |
|---|---|---|---|---|
| | No toxin | Toxin only | Toxin + antiserum | |
| Anti peptide 5–18 (6) | 0.21 ± 0.02 | 0.63 ± 0.05 | 0.27 ± 0.02 | 83 |
| Anti peptide 13–26 (4) | 0.25 ± 0.03 | 0.40 ± 0.05 | 0.30 ± 0.06 | 67 |
| Anti Shiga-toxin (4) | 0.20 ± 0.02 | 0.50 ± 0.05 | 0.22 ± 0.05 | 90 |
| Normal serum (2) | 0.20 ± 0.02 | 0.36 ± 0.05 | 0.33 ± 0.05 | 19 |

[a]Intestinal ligated loops, 2 cm long, were injected with 200 mg of: either PBS, toxin (35 mg/ml) or a mixture of the toxin and 1:25 dilution of the respective antiserum. The numbers in parenthesis designate number if loops tested.

We claim:

1. A peptide corresponding to a sequence of residues of the Shiga toxin B chain, the sequence consisting essentially of residues 5 to 18, 7 to 26, 13 to 26 or 19 to 29 of the Shiga toxin B chain, conjugated to suitable carrier.

2. A vaccine against the neurotoxin activity of Shiga toxin comprising, as active ingredient, in an amount effective to provide significant protection against the neurotoxin activity of Shiga toxin as a result of vaccination with said vaccine, a conjugated peptide as defined in claim 1.

3. A vaccine according to claim 2, wherein the carrier is a suitable toxoid.

4. A vaccine according to claim 3, where the toxoid is tetanus toxoid.

5. A vaccine according to claim 2, where the carrier is pDGDL, and where there are attached about 20 to 38 moles of peptide per mole of carrier.

6. A peptide corresponding to a sequence of residues of the Shiga toxin B chain, the sequence consisting essentially of residues 5–18, 7–26, 13–26 or 19–29 of the Shiga toxin B chain in polymeric form obtained by polymerization or interpolymerization of said residues with a suitable polymerization agent.

7. A vaccine against the neurotoxin activity of Shiga toxin comprising, as active ingredient, in an amount effective to provide significant protection against the neurotoxin activity of Shiga toxin as a result of vaccination with said vaccine, a polymeric peptide in accordance with claim 6.

8. A vaccine in accordance with claim 7 wherein said suitable polymerization agent is glutaraldehyde.

* * * * *